(12) United States Patent
Harvey et al.

(10) Patent No.: US 9,682,897 B1
(45) Date of Patent: Jun. 20, 2017

(54) HIGH DENSITY FUELS FROM OXYGENATED TERPENOIDS

(71) Applicant: The United States of America, as represented by the Secretary of the Navy, Washington, DC (US)

(72) Inventors: Benjamin G. Harvey, Ridgecrest, CA (US); Heather A. Meylemans, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 0 days.

(21) Appl. No.: 15/142,871

(22) Filed: Apr. 29, 2016

Related U.S. Application Data

(60) Provisional application No. 62/155,282, filed on Apr. 30, 2015.

(51) Int. Cl.
| | | |
|---|---|---|
| C07C 1/00 | (2006.01) | |
| C07C 5/02 | (2006.01) | |
| C10L 1/00 | (2006.01) | |
| C07C 1/24 | (2006.01) | |
| C07C 13/21 | (2006.01) | |
| C07C 13/23 | (2006.01) | |
| C10L 1/04 | (2006.01) | |

(52) U.S. Cl.
CPC .......... *C07C 1/24* (2013.01); *C07C 13/21* (2013.01); *C07C 13/23* (2013.01); *C10L 1/04* (2013.01); *C07C 2101/14* (2013.01); *C07C 2521/16* (2013.01); *C07C 2531/10* (2013.01); *C10L 2290/06* (2013.01)

(58) Field of Classification Search
CPC .......... C07C 1/00; C07C 5/02; C10L 1/00
USPC .......... 585/318, 317, 639, 275, 20, 21
See application file for complete search history.

(56) References Cited

U.S. PATENT DOCUMENTS

2013/0072730 A1* 3/2013 Knuuttila ............ C10G 45/12
585/16

* cited by examiner

*Primary Examiner* — Thuan D Dang
(74) *Attorney, Agent, or Firm* — Stuart H. Nissim

(57) ABSTRACT

A method for the efficient synthesis of useful deoxygenated terpenoids from an abundant renewable source, using catalytic conversion of oxygenated terpenoids. Oxygenated terpenoids such as 1,4-cineole and 1,8-cineole are, for example, major components of turpentine and essential oils. These oxygenated terpenoids can also be produced from sugars via a biosynthetic approach. Catalytic deoxygenation of these substrates can be used to efficiently generate commercially important chemicals and high density fuels for turbine or diesel propulsion.

14 Claims, 3 Drawing Sheets

United States Patent … US 9,682,897 B1

HIGH DENSITY FUELS FROM OXYGENATED TERPENOIDS

CROSS-REFERENCE TO RELATED APPLICATIONS

This is a non-provisional application claiming the benefit of parent application Ser. No. 62/155,282 filed on Apr. 30, 2015, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the efficient synthesis of deoxygenated terpenoids from an abundant renewable source, including embodiments using catalytic methods to efficiently convert biofeedstocks into high density biofuels.

BACKGROUND OF THE INVENTION

For more than a century, the petrochemical industry has been developing efficient methods to convert readily available hydrocarbons (oil/petroleum distillates) to oxidized molecules of interest for use as commodity chemicals, polymer precursors, plasticizers, paints, coatings, fine chemicals, and pharmaceutical synthons. As the price of oil and the environmental risks posed by its use continue to rise, a significant amount of research is now being directed toward the reverse process of how to efficiently deoxygenate complex feedstocks to generate reduced hydrocarbons.

One desirable example of this is the synthesis of full-performance renewable fuels. Cyclic terpenes are compelling feedstocks for the generation of such high performance renewable fuels; their ring structures result in higher densities and volumetric net heats of combustion compared to linear or branched-chain alkanes. Important monoterpenes for use as fuels are pure hydrocarbons such as α-pinene or limonene, but oxygenated terpenoids including ethers and alcohols may also be considered important fuel precursors. For example, 1,8-cineole, which comprises ~90% of *eucalyptus* oil, is a terpenoid ether that has been studied as a precursor to the bioaromatic compound p-cymene. Currently about 7,000 metric tons of 1,8-cineole are produced annually, but the potential worldwide annual production has been estimated at several million metric tons, with Australian capacity alone estimated at 800,000 metric tons. In addition to naturally occurring eucalyptol, 1,8-cineole and other terpenes are biosynthetic targets and a recent report has shown that 1,8-cineole can be generated from biomass sources by the fungus *Hypoxylon* sp. The use of fungi and other organisms that can convert crude biomass sources into terpenoids like 1,8-cineole has the potential to greatly reduce the cost, and increase the availability, of these renewable hydrocarbons.

Along with 1,8-cineole, a host of oxygenated terpenoids can be obtained from plant distillates. For example, hydro-distilled pine oil from *Pinus armandii* in Southwest China is composed of 33% oxygenated terpenoids. Solvent grade gum spirit turpentine can contain roughly 10% of a mixture of 1,4- and 1,8-cineole. Crude sulfate turpentine (CST)—which represents the bulk of commercial terpene production—typically contains small but important amounts of oxygenated terpenoids. For example, CST produced in the southern United States contains about 3-7% oxygenated terpenoids, while western mills generate CST with 8-20% oxygenated hydrocarbons. In contrast, other low-grade turpentines produced by the paper industry and called "red oils" are highly oxygenated due to treatment with aqueous acid solutions to promote distillation of mercaptans and recovery of methanol. This red oil is currently considered a waste product and is typically disposed of by incineration.

The conversion of 1,8-cineole to the bioaromatic p-cymene with transition metal doped gamma alumina was recently described, as was the isomerization of α-terpineol to 1,4- and 1,8-cineole with $H_3PW_{12}O_{40}$. Homogenous systems have also been explored. For example, the hydration of α-pinene and CST with dilute sulfuric acid to generate α-terpineol and other terpene isomers has been studied. The reverse reaction, dehydration of α-terpineol with aqueous oxalic acid, was examined in 1961.

Although oxygenated terpenes such as cineoles and α-terpineol are desirable for fragrance, flavor, and antiseptic applications, the complicated distribution of products in crude feedstocks such as red turpentine oil make these mixtures much less valuable for specialty applications and therefore more intriguing for the production of renewable fuels

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

This disclosure describes processes for the selective deoxygenation of terpenoid ethers and alcohols to generate deoxygenated terpenoids, preferably having the formula $C_{10}H_{16}$. The resulting deoxygenated terpenoids can be used, or converted to be used, for example, as a variety of high density fuels, fuel additives, terpene dimers and purified menthadienes. Fuels containing deoxygenated terpenoid derivatives have significantly higher densities and volumetric net heats of combustion than conventional petroleum-based fuels or biofuels.

Figure 1:
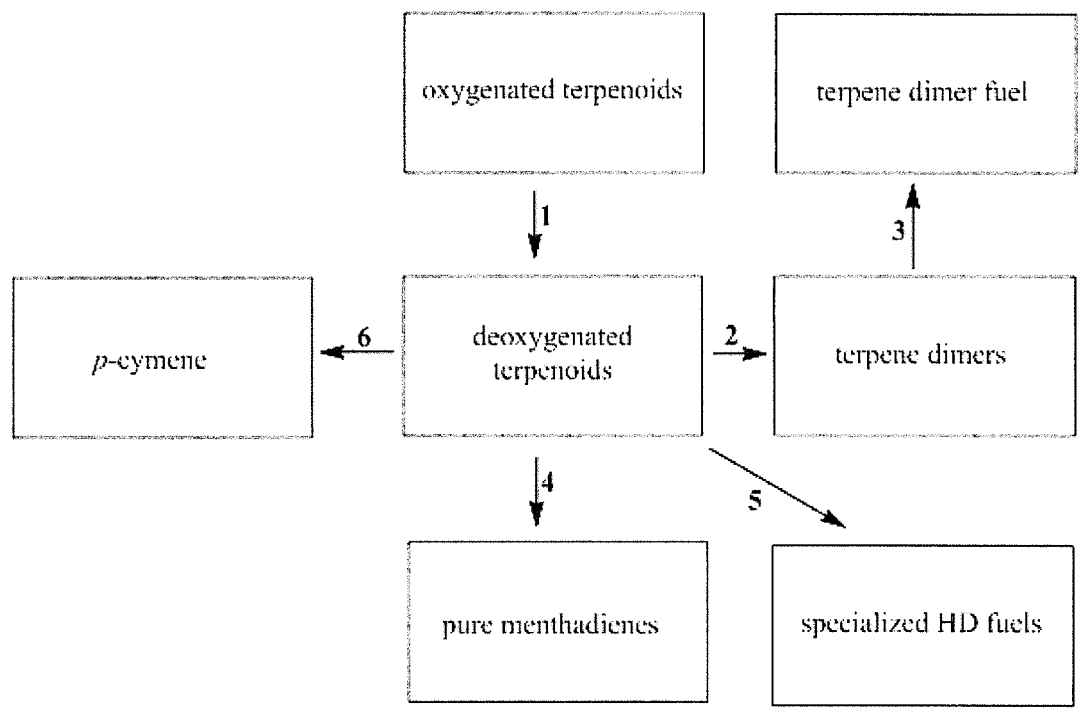
FIG. 1 is an illustration of synthetic schemes for producing fuels, fuel additives, and deoxygenated terpenoids from oxygenated terpenoids according to embodiments of the invention.
Figure 2:
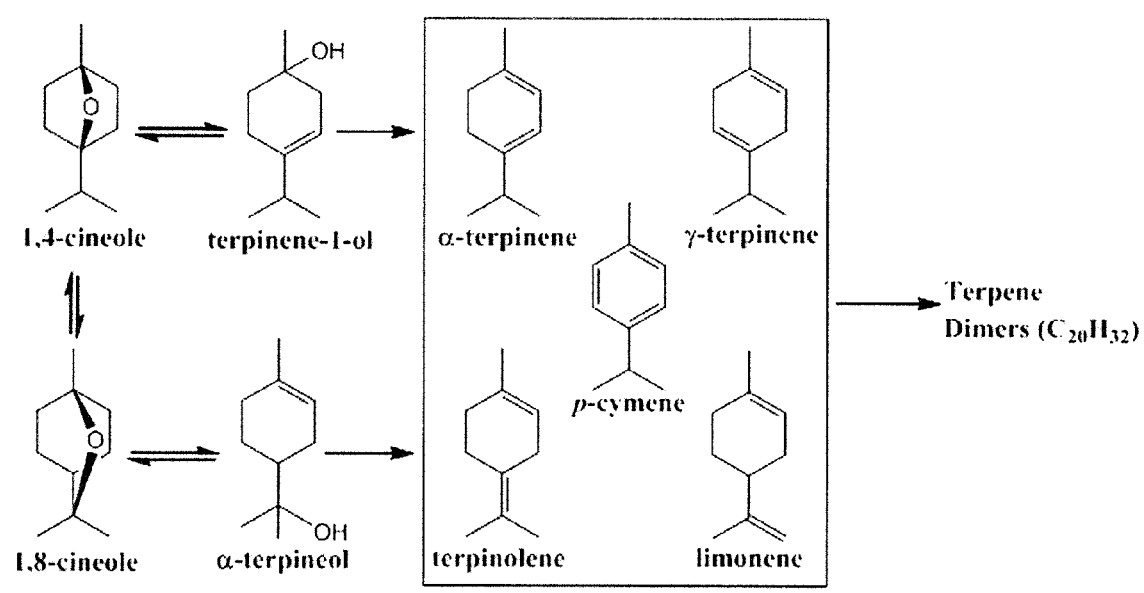
FIG. 2 is an illustration of synthetic schemes for producing terpene dimers as precursors to fuels using a renewable oxygenated terpenoid source according to embodiments of the invention.

Preferred processes of the current invention allow for various oxygenated terpenoids to be converted to high density fuels. Embodiments of the invention comprise the following processes, as illustrated in FIG. 1: oxygenated terpenoids are allowed to react with catalysts to generate deoxygenated terpenoids.

In a variety of preferred embodiments the deoxygenated terpenoids are further processed. For example, terpenes are directly (single-pot or gas phase) converted to terpene dimers with deoxygenation catalysts. These terpene dimers are then hydrogenated and purified by fractional distillation to generate high density renewable fuels or traction fluids. In embodiments the hydrogenation is conducted in a temperature range from about 20° C. to about 200° C. and at hydrogen pressures ranging between 1 and 50 atmospheres. In embodiments the hydrogenation is conducted with a heterogeneous catalyst comprised of supported transition metals including, but not limited to, Ni, Pd, Pt, Ru, Rh, Cu, and Cr. The hydrogenated terpene dimers are then separated by fractional distillation under reduced pressure.

In another embodiment, deoxygenated terpenoids can be separated by fractional distillation to generate pure molecules, for example, flavor and fragrance additives.

In yet another embodiment, conjugated terpenes are allowed to react with other olefins in the presence of a Diels Alder catalyst to generate high density fuels. This reaction is conducted at temperatures ranging from about 100° C. up to about 350° C. Preferred Diels Alder catalysts are Lewis acids.

In a further embodiment, deoxygenated terpenoids are allowed to react with a dehydrogenation catalyst to yield p-cymene which can be blended with jet fuel or utilized in high octane gasoline formulations.

The deoxygenation of cineoles is of significant interest for the efficient conversion of crude, oxygenated terpenoid feedstocks to high density diesel fuels. These deoxygenated terpenoids can be converted to terpene dimers with the oxygen being removed as water. According to a preferred process of the present invention the catalyzed conversion of monoterpenes yields high density hydrogenated diterpenes that have net heats of combustion in the range of 135,000 btu/gal up to 145,000 btu/gal and densities ranging between about 0.90 g/mL and about 0.95 g/mL. Preferred hydrogenated diterpenes have net heats of combustion of greater than 141,000 btu/gal and densities on the order of 0.94 g/mL. Such diterpenes can be used as high density missile fuels; their relatively high average molecular weight and viscosity also makes them suitable as blending components with diesel range fuels.

In preferred processes of the present invention various sources of oxygenated terpenoids can be used. While pure terpenes can be used as substrates, preferably, more cost effective feedstocks containing a mixture of terpenoids are used. Suitable feedstocks include, but are not limited to, *eucalyptus* oil, hydrodistilled pine oil, solvent grade gum spirit turpentine, crude sulfate turpentine, and low-grade turpentines produced by the paper industry often referred to as "red oils". For example, gum turpentine distillate often contains a mixture of α-pinene, camphene, and oxygenated terpenoids including terpenoid ethers and terpenoid alcohols. In preferred embodiments the feedstock contains significant quantities of 1,4-cineole and 1,8-cineole.

Preferred oxygenated terpenoids such as 1,4-cineole and 1,8-cineole can be major components of turpentine and essential oils. These terpenoids can also be produced from sugars via a biosynthetic approach. The catalytic deoxygenation of these substrates according to the processes of the present invention can be used to efficiently generate commercially important chemicals and high density fuels for turbine or diesel propulsion. This present invention shows the great potential of heterogeneous acid catalysts to effectively convert oxygenated terpenoids to high density hydrocarbon mixtures with potential uses as renewable diesel fuels.

In preferred embodiments, the low-temperature deoxygenation reactions are performed over a catalyst. A preferred embodiment utilizes a heterogeneous acid catalyst. Examples of preferred catalysts include, but are not limited to, acid catalysts, zeolites, aluminosilicates, clays, cation exchange resins, sulfated zirconia, sulfated titania, other metal oxides, and any combination thereof. Preferred catalysts used in the Examples include, Nafion® SAC-13 (E. I. du Pont de Nemours & Co., Inc., Wilmington, Del., USA), Amberlyst®15 (The Dow Chemical Company, Midland, Mich., USA), and Montmorillonite K10 (MMT-K10).

In one embodiment, the process is performed using a solvent. Examples of preferred solvents include, but are not limited to: aprotic hydrocarbon solvents including alkanes (e.g. heptane, octane, nonane, cyclohexane, methylcyclohexane, other alkyl cyclohexanes); aromatic solvents including benzene, toluene, xylenes; ethers; and cyclic ethers. In preferred embodiments the solvent has a boiling point in the range of about 80-150° C. In other embodiments the reaction temperature can be controlled by the reflux temperature of the solvent.

According to the present invention, the dehydration of cineoles as components of complex terpenoid mixtures and subsequent conversion to dimer molecules is performed at temperatures ranging from ambient to about 170° C., but more preferably between about 80 and 120° C.

In preferred embodiments the dehydration of cineoles is conducted with substrate:catalyst ratios ranging between about 1,000,000:1 and 2:1.

In another embodiment, the process is performed in a continuous fashion using a flow reactor.

In yet another embodiment, the process is performed in the gas phase

For the following examples, 1,4-cineole, 1,8-cineole, Amberlyst® 15, Nafion® SAC-13, and MMT-K10 were all purchased from Aldrich and used without purification. Gas chromatography standards for α-terpinene, γ-terpinene, p-cymene, limonene, and terpinolene were purchased from Aldrich and used as received. α-terpineol was purchased from Acros Chemical Co. and used as received.

For the following examples, gas chromatography (GC-MS) was carried out on an Agilent 6890N GC using a Restek Rxi-5 ms 20 m×0.18 mm i.d. capillary column with a 0.18 μm coating of Crossbond 5% diphenyl/95% dimethyl polysiloxane. The GC was programmed from 40 to 100° C. at 5° C./min and then 100 to 300° C. at 20° C./min. The GC detector was an Agilent 5973N mass selective detector (MSD). The samples were prepared with approximately 10 mg of sample, accurately weighed, and diluted with 10 mL hexanes. A series of five calibration standards were prepared with concentrations ranging from approximately 10-100 ppm. The samples and standards were injected three times and the peak areas averaged. A linear calibration curve was generated from the calibration standards and used to quantify the samples. Ions were selected for each compound for peak area quantification, enabling resolution and quantification of compounds with similar elution times, such as 1,4-cineole/α-terpinene and limonene/eucalyptol For the following examples, GC/FID was carried out on an Agilent 820A equipped with a flame ionization detector and using an Agilent J&W HP-5 30 m×0.32 mm i.d. capillary column with a 0.25 μm coating of Crossbond 5% diphenyl/95% dimethyl polysiloxane. The GC oven was ramped from 40 to 100° C. at 2° C./min and then 100 to 300° C. at 20° C./min. Samples (0.1 μL) of fluid (0.1 mL neat terpenes in 10 mL hexanes) were injected via syringe into a split/splitless injector set to a 50 to 1 split ratio.

All of the samples were run on the GC-MS and products were determined using NIST library matches. Commercially available pure standards of the molecules of interest (except for terpinolene-1-ol) were then run on the GC-MS to verify the retention times and assignment of the peaks. The same standards were then run on the GC 7820A instrument to obtain comparable retention times. Good agreement was seen between the two instruments for the order of elution of the various compounds. All samples were then run on the GC/FID to get ion counts for each of the products. The information from the GC/MS analysis was then used in conjunction with the total ion count from the GC-FID instrument to determine the total % area for these two compounds.

Example 1

The deoxygenation and dimerization of representative terpenoid ethers utilized 1,4-cineole and 1,8-cineole as feedstocks. Relatively high conversion efficiencies in a convenient time frame were achieved using a low reaction temperature of 85° C. Three solid acid catalysts were used; Nafion® SAC-13, Amberlyst® 15, and MMT-K10.

Results from the Example are illustrated in Table 1.

TABLE 1

Reactivity of heterogeneous acid catalysts with cineoles

| Catalyst | Substrate | Initial Activity (at 2 h, g sub/(g cat * h) | Conversion (% at 24 h) | Dimer (% at 24 h) |
|---|---|---|---|---|
| Amberlyst-15 | 1,4-cineole | 5.8 | 100 | 59 |
| Nafion SAC-13 | 1,4-cineole | 5.0 | 90 | 2 |
| MMT-K10 | 1,4-cineole | 1.5 | 85 | 1 |
| Amberlyst-15 | 1,8-cineole | 5.8 | 83 | 47 |
| Nafion SAC-13 | 1,8-cineole | 1.3 | 70 | 7 |
| MMT-K10 | 1,8-cineole | 0.3 | 38 | 4 |

Conditions: 85° C., no solvent, 5 g of substrate, 250 mg of catalyst.

Example 2

In this example, 1,4-cineole (5 g, 33 mmol) was allowed to react with 250 mg of the catalyst Amberlyst® 15 (The Dow Chemical Company). The mixture was stirred at 85° C. under nitrogen for 24 hours. 100 μL samples were removed from the reaction mixture via syringe at 2, 4, 6, 8, and 24 hours. The samples were analyzed using gas chromatography.

Table 2 shows the results of the conversion process utilizing 1,4-cineole as the substrate. The table shows the product distribution (as a percentage of the total) of 1,4-cineole isomerization reaction at 2, 4, 6, 8, and 24 hours. Table 2. 1,4-Cineole reacted with Amberlyst®15 [Conditions: (catalyst:substrate=1:20 (by mass), 85° C.)]

TABLE 2

1,4-Cineole reacted with Amberlyst ® 15

| Products | 2 h | 4 h | 6 h | 8 h | 24 h |
|---|---|---|---|---|---|
| 1,4-cineole | 42 | 25 | 17 | 11 | 0 |
| 1,8-cineole | 2 | 2 | 2 | 3 | 0 |
| α-terpinene | 13 | 20 | 23 | 29 | 16 |
| γ-terpinene | 19 | 24 | 28 | 30 | 5 |
| limonene | 2 | 3 | 2 | 2 | 1 |
| p-cymene | 3 | 4 | 3 | 3 | 5 |
| terpinolene | 11 | 14 | 16 | 17 | 10 |
| terpinene-1-ol | 5 | 3 | 1 | 1 | 0 |
| dimer | 1 | 1 | 4 | 1 | 59 |
| TOTAL | 98 | 96 | 96 | 97 | 96 |

[Conditions: (catalyst:substrate = 1:20 (by mass), 85° C.)]

Example 3

In this example, 1,4-cineole (5 g, 33 mmol) was allowed to react with 250 mg of the catalyst Nafion® SAC-13 (DuPont). The mixture was stirred at 85° C. under nitrogen for 24 hours. 100 μL samples were removed from the reaction mixture via syringe at 2, 4, 6, 8, and 24 hours. The samples were analyzed using gas chromatography.

Table 3 shows the results of the conversion process utilizing 1,4-cineole as the substrate. The table shows the product distribution (as a percentage of the total) of 1,4-cineole isomerization reaction at 2, 4, 6, 8, and 24 hours.

Table 3. 1,4-Cineole reacted with Nafion® Sac-13

TABLE 3

1,4-Cineole reacted with Nafion ® Sac-13

| Products | 2 h | 4 h | 6 h | 8 h | 24 h |
|---|---|---|---|---|---|
| 1,4-cineole | 50 | 50 | 42 | 37 | 10 |
| 1,8-cineole | 1 | 1 | 1 | 1 | 2 |
| α-terpinene | 15 | 15 | 22 | 26 | 51 |
| γ-terpinene | 10 | 11 | 11 | 11 | 13 |
| limonene | 2 | 2 | 2 | 2 | 2 |
| p-cymene | 3 | 3 | 4 | 4 | 3 |
| terpinolene | 8 | 9 | 9 | 9 | 10 |
| terpinene-1-ol | 5 | 5 | 5 | 5 | 4 |
| Dimer | 2 | 1 | 0 | 1 | 1 |
| TOTAL | 96 | 97 | 96 | 96 | 96 |

Example 4

In this example, 1,4-cineole (5 g, 33 mmol) was allowed to react with 250 mg of the catalyst MMT-K10. The mixture was stirred at 85° C. under nitrogen for 24 hours. 100 μL samples were removed from the reaction mixture via syringe at 2, 4, 6, 8, and 24 hours. The samples were analyzed using gas chromatography.

Table 4 shows the results of the conversion process utilizing 1,4-cineole as the substrate. The table shows the product distribution (as a percentage of the total) of 1,4-cineole isomerization reaction at 2, 4, 6, 8, and 24 hours.

Table 4. 1,4-Cineole reacted with MMT-K10

TABLE 4

1,4-Cineole reacted with MMT-K10

| Products | 2 h | 4 h | 6 h | 8 h | 24 h |
|---|---|---|---|---|---|
| 1,4-cineole | 85 | 75 | 69 | 66 | 15 |
| 1,8-cineole | 0 | 1 | 1 | 1 | 1 |
| α-terpinene | 7 | 13 | 15 | 16 | 59 |
| γ-terpinene | 1 | 1 | 1 | 3 | 8 |
| limonene | 0 | 0 | 0 | 1 | 1 |
| p-cymene | 1 | 3 | 5 | 2 | 2 |
| terpinolene | 1 | 1 | 1 | 2 | 6 |
| terpinene-1-ol | 1 | 2 | 3 | 3 | 4 |
| Dimer | 0 | 0 | 3 | 4 | 2 |
| TOTAL | 96 | 96 | 98 | 98 | 98 |

Example 5

In this example, 1,8-cineole (5 g, 33 mmol) was allowed to react with 250 mg of the catalyst Amberlyst® 15 (The Dow Chemical Company). The mixture was stirred at 85° C. under nitrogen for 24 hours. 100 µL samples were removed from the reaction mixture via syringe at 2, 4, 6, 8, and 24 hours. The samples were analyzed using gas chromatography.

Table 5 shows the results of the conversion process utilizing 1,8-cineole as the substrate. The table shows the product distribution (as a percentage of the total) of 1,8-cineole isomerization reaction at 2, 4, 6, 8, and 24 hours.

Table 5. 1,8-Cineole reacted with Amberlyst® 15 [Conditions: (catalyst:substrate=1:20, 85° C.)]

TABLE 5

1,8-Cineole reacted with Amberlyst® 15

| Products | 2 h | 4 h | 6 h | 8 h | 24 h |
|---|---|---|---|---|---|
| 1,4-cineole | 10 | 3 | 2 | 1 | 0 |
| 1,8-cineole | 46 | 43 | 39 | 39 | 17 |
| α-terpinene | 5 | 11 | 17 | 18 | 11 |
| γ-terpinene | 10 | 10 | 13 | 13 | 7 |
| limonene | 3 | 8 | 7 | 7 | 4 |
| p-cymene | 4 | 4 | 2 | 2 | 0 |
| terpinolene | 18 | 17 | 19 | 19 | 11 |
| terpinene-1-ol | 2 | 1 | 0 | 0 | 0 |
| Dimer | 1 | 3 | 1 | 1 | 47 |
| TOTAL | 99 | 100 | 100 | 100 | 97 |

[Conditions: (catalyst:substrate = 1:20, 85° C.)]

Example 6

In this example, 1,8-cineole (5 g, 33 mmol) was allowed to react with 250 mg of the catalyst Nafion® SAC-13 (DuPont). The mixture was stirred at 85° C. under nitrogen for 24 hours. 100 µL samples were removed from the reaction mixture via syringe at 2, 4, 6, 8, and 24 hours. The samples were analyzed using gas chromatography.

Table 6 shows the results of the conversion process utilizing 1,8-cineole as the substrate. The table shows the product distribution (as a percentage of the total) of 1,8-cineole isomerization reaction at 2, 4, 6, 8, and 24 hours.

Table 6. 1,8-Cineole reacted with Nafion® Sac-13

TABLE 6

1,8-Cineole reacted with Nafion® Sac-13

| Products | 2 h | 4 h | 6 h | 8 h | 24 h |
|---|---|---|---|---|---|
| 1,4-cineole | 0 | 3 | 2 | 2 | 0 |
| 1,8-cineole | 89 | 78 | 65 | 54 | 31 |
| α-terpinene | 1 | 1 | 6 | 9 | 26 |
| γ-terpinene | 0 | 2 | 4 | 5 | 15 |
| limonene | 7 | 7 | 11 | 14 | 0 |
| p-cymene | 0 | 1 | 1 | 1 | 1 |
| terpinolene | 2 | 7 | 12 | 14 | 21 |
| terpinene-1-ol | 0 | 0 | 0 | 0 | 0 |
| Dimer | 1 | 1 | 1 | 1 | 4 |
| TOTAL | 100 | 100 | 102 | 100 | 98 |

Example 7

In this example, 1,8-cineole (5 g, 33 mmol) was allowed to react with 250 mg of the catalyst MMT-K10. The mixture was stirred at 85° C. under nitrogen for 24 hours. 100 µL samples were removed from the reaction mixture via syringe at 2, 4, 6, 8, and 24 hours. The samples were analyzed using gas chromatography.

Table 7 shows the results of the conversion process utilizing 1,8-cineole as the substrate. The table shows the product distribution (as a percentage of the total) of 1,8-cineole isomerization reaction at 2, 4, 6, 8, and 24 hours.

Table 7. 1,8-Cineole reacted with MMT-K10

TABLE 7

1,8-Cineole reacted with MMT-K10

| Products | 2 h | 4 h | 6 h | 8 h | 24 h |
|---|---|---|---|---|---|
| 1,4-cineole | 0 | 0 | 0 | 1 | 3 |
| 1,8-cineole | 98 | 95 | 90 | 86 | 63 |
| α-terpinene | 0 | 0 | 1 | 1 | 8 |
| γ-terpinene | 0 | 0 | 0 | 1 | 4 |
| limonene | 1 | 4 | 6 | 6 | 1 |
| p-cymene | 0 | 0 | 1 | 1 | 0 |
| terpinolene | 0 | 0 | 2 | 3 | 13 |
| terpinene-1-ol | 0 | 0 | 0 | 0 | 0 |
| Dimer | 0 | 0 | 1 | 1 | 7 |
| TOTAL | 99 | 99 | 101 | 100 | 99 |

Example 8

In this example, oxygenated terpenoids were allowed to react with the catalyst in n-heptane. The mixture was stirred at 85° C. under nitrogen for 24 hours. 100 µL samples were removed from the reaction mixture via syringe at 2, 4, 6, 8, and 24 hours. The samples were analyzed using gas chromatography.

Example 9

In this example, terpene dimers are hydrogenated and purified by fractional distillation to generate high density products which can be used as renewable fuels or traction fluids. The hydrogenation is conducted in a temperature range of from ambient to about 200° C. and at hydrogen pressure ranging between 1 and 50 atmospheres. The hydrogenation is conducted with a heterogeneous catalyst comprised of supported transition metals including Ni, Pd, Pt, Ru, Rh, Cu, and Cr. The hydrogenated terpene dimers are then separated by fractional distillation under reduced pressure.

As illustrated in the Examples, Amberlyst® 15 was an active catalyst on a weight basis, giving 100% conversion of 1,4-cineole after 24 hours with an initial activity of 5.8 g substrate/(g·cat·h). 59% of the product was dimer molecules with the bulk of the remaining products consisting of deoxygenated terpenes. Nafion® SAC-13 allowed for 90% conversion of 1,4-cineole and had an initial activity (5 g substrate/(g·cat·h)) similar to Amberlyst® 15, but the conversion to dimer was only 2%.

Figure 3:
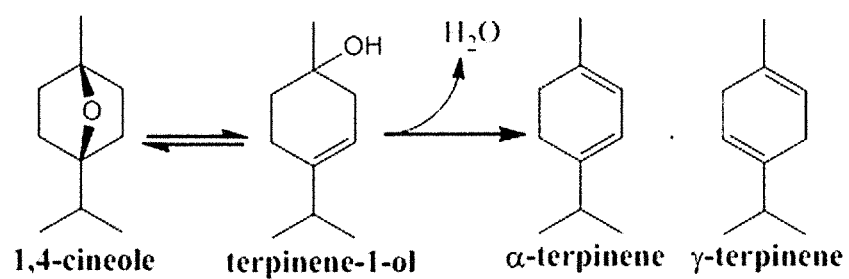
FIG. 3 is an illustration of a synthetic scheme for producing deoxygenated terpenoids as precursors to fuels using 1,4-cineole as a terpene source according to embodiments of the invention.

As illustrated in FIG. 3, the 1,4-cineole was found to isomerize to terpinene-1-ol followed by dehydration to a mixture primarily composed of α- and γ-terpinene. In a similar manner, 1,8-cineole was found to isomerize to α-terpineol followed by dehydration to primarily terpinolene and α-terpinene (see FIG. 4). In the case of 1,4-cineole, the main product for the Nafion® SAC-13 and MMT-K10 catalyzed reactions is α-terpinene (>50% at 8 h for Nafion®) followed by moderate amounts of γ-terpinene and terpinolene (Table 3). In contrast, the Amberlyst-catalyzed reaction results in nearly equal concentrations of α- and γ-terpinene. Terpinene-1-ol was also observed but not as a significant product with all three catalysts. See FIG. 3.

Figure 4:
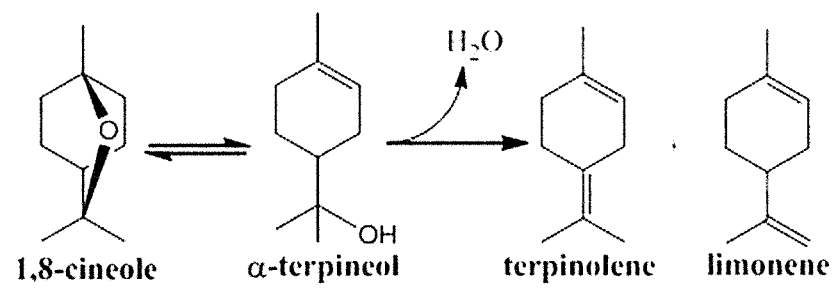
FIG. 4 is an illustration of a synthetic scheme for producing deoxygenated terpenes as precursors to fuels using 1,8-cineole as a terpene source according to embodiments of the invention.

As illustrated in FIG. 4, when 1,8-cineole was used as a substrate the same products were observed, but the product distribution was markedly different. In particular, the relative amounts of terpinolene and limonene were significantly higher. When Amberlyst-15 was used as the catalyst, the most abundant monoterpene was terpinolene, followed by α- and γ-terpinene. Contrary to the results obtained with 1,4-cineole, no terpinene-1-ol is observed. Instead, α-terpineol appears to be the primary alcohol intermediate for the reaction. This is consistent with the structure of 1,8-cineole which has the oxygen bridging to the central carbon of the exocyclic isopropylidene group. Based on the product distribution it appears that 1,8-cineole isomerizes first to α-terpineol which is then dehydrated to give primarily terpinolene and limonene.

At early reaction times the 1,4-cineole reaction mixture contains small amounts of 1,8-cineole showing that the acid catalysts promote isomerization of the two substrates. In a similar manner the 1,8-cineole reaction mixtures contain a significant amount of 1,4-cineole. The equilibrium between the two terpenoid ethers then opens up both reaction pathways. The product distribution is further altered by subsequent isomerization of the deoxygenated terpenoids. For example, when Nafion® SAC-13 is used as the catalyst, a higher percentage of terpinenes are present In one preferred embodiment, this process can be conducted stepwise chronologically to selectively produce deoxygenated products with well-defined reactivity. The process can be halted at an appropriate time to increase the yield of a desired product.

The stepwise process can be used, for example, to produce another product of interest; p-cymene which is derived from the dehydrogenation of the terpene intermediates. Although present as a minor product in most of the reactions, it was a significant product in the MMT-K10 catalyzed deoxygenation of 1,4-cineole. No evidence of menthenes was found in the GC suggesting that a direct dehydrogenation reaction occurs. In addition, the amount of p-cymene increases to a maximum at 6 h and then decreases.

In addition to the broad applications, deoxygenation reactions of terpenoid ethers may be used for formal syntheses of specific terpenes. For example, deoxygenation of 1,4-cineole with Nafion® SAC-13 was highly selective for α-terpinene.

The present process describes a sustainable method for the synthesis of renewable fuels and conforms to many of the tenets of green chemistry. The present process requires only modest energy inputs, can be conducted without a solvent, and utilizes non-corrosive, heterogeneous catalysts. The application of this process to crude oxygenated terpenoid mixtures is expected to greatly expand the utility of these biofeedstocks.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A low temperature process for producing deoxygenated terpenoids comprising: providing a renewable feedstock comprised of at least one oxygenated cyclic terpene;
   wherein said at least one oxygenated cyclic terpene is comprised of a terpenoid ether, a terpenoid alcohol, or combinations thereof;
   deoxygenating said at least one oxygenated cyclic terpene with a catalyst at a temperature up to about 170° C. to produce said deoxygenated terpenoids;
   isolating said deoxygenated terpenoids; wherein said deoxygenated terpenoids comprise one or more terpene dimers;
   hydrogenating said deoxygenated terpenoids to generate hydrogenated deoxygenated terpenoids comprising hydrogenated terpene dimers; and
   wherein said hydrogenated terpene dimers have net heats of combustion ranging from about 135,000 Btu/gal up to about 145,000 Btu/gal and densities ranging from about 0.90 g/mL up to about 0.95 g/mL.

2. The process of claim 1 wherein said deoxygenated terpenoids further comprise one or more cyclic terpenes.

3. The process of claim 1 wherein said renewable feedstock comprises 1,4-cineole, 1,8-cineole, *eucalyptus* oil, hydrodistilled pine oil, gum spirit turpentine, crude sulfate turpentine, red oils or combinations thereof.

4. The process of claim 1 wherein said catalyst is a heterogeneous acid catalyst.

5. The process of claim 4 wherein said catalyst is selected from the group consisting of zeolites, aluminosilicates, clays, cation exchange resins, sulfated zirconia, sulfated titania, metal oxides, and combinations thereof.

6. The process of claim 1 wherein the process is performed at a temperature ranging from about 20° C. to about 100° C.

7. The process of claim 1 wherein said deoxygenated terpenoids are isolated using fractional distillation.

8. The process of claim 1 wherein the process is performed in a continuous fashion using a flow reactor.

9. The process of claim 1 wherein the process is performed in the gas phase.

10. The process of claim 1 wherein said deoxygenated terpenoids further comprise p-cymene, α-terpinene, γ-terpinene, or combinations thereof.

11. The process of claim 1 wherein said process utilizes a solvent comprising aprotic hydrocarbon solvents, aromatic solvents, ethers, cyclic ethers, and combinations thereof.

12. The process of claim 11 wherein said solvent has a boiling point in the range of about 80° C. to about 150° C.

13. The process of claim 11 wherein said solvent comprises heptane, octane, nonane, other acyclic alkanes, cyclohexane, methylcyclohexane, other alkyl cyclohexanes, benzene, toluene, xylenes, ethers, cyclic ethers or combinations thereof.

14. The process of claim 1 wherein said process is conducted without a solvent.

* * * * *